United States Patent
Umekawa

(10) Patent No.: US 11,399,796 B2
(45) Date of Patent: Aug. 2, 2022

(54) RADIATION IMAGING SYSTEM COMPRISING RADIATION IMAGING APPARATUS CONFIGURED TO INDICATE A DEFECTIVE PIXEL AND METHOD OF CONTROLLING RADIATION IMAGING APPARATUS

(71) Applicant: CANON KABUSHIKI KAISHA, Tokyo (JP)

(72) Inventor: Kazuaki Umekawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 16/775,091

(22) Filed: Jan. 28, 2020

(65) Prior Publication Data

US 2020/0252562 A1  Aug. 6, 2020

(30) Foreign Application Priority Data

Feb. 6, 2019 (JP) .............................. JP2019-019733

(51) Int. Cl.
*A61B 6/00* (2006.01)
*G01T 1/20* (2006.01)
(Continued)

(52) U.S. Cl.
CPC ................ *A61B 6/585* (2013.01); *A61B 6/42* (2013.01); *A61B 6/4208* (2013.01); *A61B 6/4233* (2013.01); *A61B 6/4241* (2013.01); *A61B 6/486* (2013.01); *A61B 6/487* (2013.01); *A61B 6/52* (2013.01); *A61B 6/5205* (2013.01);
(Continued)

(58) Field of Classification Search
CPC ....... A61B 6/42; A61B 6/4208; A61B 6/4233; A61B 6/486; A61B 6/487; A61B 6/52; A61B 6/5205; A61B 6/5211; A61B 6/5241; A61B 6/54; A61B 6/542; A61B 6/545; A61B 6/58; A61B 6/585; A61B 6/586;
(Continued)

(56) References Cited

U.S. PATENT DOCUMENTS 5,970,115 A * 10/1999 Colbeth .................. H04N 5/367
                                                    348/E5.081
6,201,249 B1 * 3/2001 Yamayoshi .......... A61B 6/4494
                                                    250/370.11
(Continued)

FOREIGN PATENT DOCUMENTS

JP      2009-219691 A   10/2009
JP      2014-66689 A    4/2014
JP      2014-068881 A   4/2014

*Primary Examiner* — Allen C. Ho
(74) *Attorney, Agent, or Firm* — Canon U.S.A., Inc. IP Division

(57) ABSTRACT

Provided is a technology with which defective pixel information in taking a radiation image and defective pixel information in detecting a dose can be generated efficiently. Provided is a radiation imaging apparatus including: a plurality of pixels arranged to convert radiation into an electric signal; and a generation unit configured to generate, based on the electric signal obtained as a result of a conversion by the plurality of pixels, first defective pixel information indicating a defective pixel in taking a radiation image among the plurality of pixels, and second defective pixel information indicating a defective pixel in detecting a dose among the plurality of pixels.

20 Claims, 6 Drawing Sheets

(51) Int. Cl.
  *G01T 1/24* (2006.01)
  *H04N 5/32* (2006.01)
  *H04N 5/367* (2011.01)

(52) U.S. Cl.
  CPC .......... *A61B 6/5211* (2013.01); *A61B 6/5241* (2013.01); *A61B 6/54* (2013.01); *A61B 6/542* (2013.01); *A61B 6/545* (2013.01); *A61B 6/58* (2013.01); *A61B 6/586* (2013.01); *G01T 1/2006* (2013.01); *G01T 1/2018* (2013.01); *G01T 1/24* (2013.01); *H04N 5/32* (2013.01); *H04N 5/367* (2013.01)

(58) Field of Classification Search
  CPC ... A61B 6/4241; G01T 1/2018; G01T 1/2006; G01T 1/24; H04N 5/32; H04N 5/367
  USPC .............. 378/19, 98.8, 207; 250/370.09
  See application file for complete search history.

(56) References Cited

U.S. PATENT DOCUMENTS

| | | | | |
|---|---|---|---|---|
| 6,320,934 | B1 * | 11/2001 | Carroll | H04N 5/3651 348/E5.037 |
| 6,354,737 | B1 * | 3/2002 | Hute | H04N 5/32 378/165 |
| 6,381,374 | B1 * | 4/2002 | Pourjavid | H04N 5/367 348/E5.081 |
| 6,418,241 | B1 * | 7/2002 | Schreiner | H04N 5/3651 378/98.2 |
| 6,497,511 | B1 * | 12/2002 | Schmitt | H04N 5/325 378/207 |
| 6,512,217 | B1 * | 1/2003 | Kameshima | H01L 27/14676 348/300 |
| 6,515,285 | B1 * | 2/2003 | Marshall | H04N 5/367 250/339.04 |
| 6,529,618 | B1 * | 3/2003 | Ohara | H04N 5/325 382/141 |
| 6,529,622 | B1 * | 3/2003 | Pourjavid | H04N 5/367 348/E5.081 |
| 6,623,161 | B2 * | 9/2003 | Aufrichtig | A61B 6/5258 378/207 |
| 9,194,964 | B2 * | 11/2015 | Ito | H04N 5/367 |
| 9,201,149 | B2 * | 12/2015 | Ben Hayun | G01T 1/2018 |
| 9,625,585 | B1 * | 4/2017 | Yokoyama | G01T 1/023 |
| 9,833,214 | B2 * | 12/2017 | Imamura | H01L 27/14812 |
| 10,342,508 | B2 * | 7/2019 | Matsushita | A61B 6/566 |
| 10,368,823 | B2 * | 8/2019 | Uchiyama | A61B 6/4266 |
| 10,404,929 | B2 * | 9/2019 | Nishino | H04N 5/357 |
| 10,420,524 | B2 * | 9/2019 | Yamada | A61B 6/4266 |
| 10,448,914 | B2 * | 10/2019 | Spahn | H04N 5/335 |
| 10,466,373 | B2 * | 11/2019 | Ohguri | H04N 5/3651 |
| 10,695,024 | B2 * | 6/2020 | Miyamoto | G06T 5/009 |
| 10,751,020 | B2 * | 8/2020 | Konno | A61B 6/586 |
| 10,779,777 | B2 * | 9/2020 | Terui | A61B 6/032 |
| 10,785,424 | B2 * | 9/2020 | Kanamori | H04N 5/345 |
| 10,813,617 | B2 * | 10/2020 | Inoue | A61B 6/06 |
| 10,830,910 | B2 * | 11/2020 | Ishii | H04N 5/378 |
| 10,914,849 | B2 * | 2/2021 | Ofuji | H04N 5/32 |
| 10,939,884 | B2 * | 3/2021 | Nariyuki | A61B 6/58 |
| 10,992,885 | B2 * | 4/2021 | Iwakiri | H04N 5/32 |
| 11,000,701 | B2 * | 5/2021 | Lu | A61N 5/1048 |
| 11,026,650 | B2 * | 6/2021 | Duewer | A61B 6/5235 |
| 11,039,805 | B2 * | 6/2021 | De Man | G06N 3/08 |
| 11,064,966 | B2 * | 7/2021 | Iwakiri | A61B 6/56 |
| 11,092,698 | B2 * | 8/2021 | Tanaka | G01T 1/20 |
| 11,099,141 | B2 * | 8/2021 | Yamakawa | G01N 23/04 |
| 11,122,221 | B2 * | 9/2021 | Cao | G11C 29/76 |
| 11,157,059 | B2 * | 10/2021 | Yokoyama | G01T 1/17 |
| 11,179,115 | B2 * | 11/2021 | Konno | G06T 11/003 |
| 11,199,637 | B2 * | 12/2021 | Kobayashi | A61B 6/40 |
| 11,206,366 | B2 * | 12/2021 | Iwakiri | G01T 7/00 |
| 11,213,261 | B2 * | 1/2022 | Takahashi | A61B 6/5241 |
| 11,213,271 | B2 * | 1/2022 | Tachikawa | A61B 6/548 |
| 11,219,114 | B2 * | 1/2022 | Kuwata | G01N 23/04 |
| 2013/0126742 | A1 | 5/2013 | Hayun | |
| 2014/0084175 | A1 | 3/2014 | Ito | |

\* cited by examiner

RADIATION IMAGING SYSTEM COMPRISING RADIATION IMAGING APPARATUS CONFIGURED TO INDICATE A DEFECTIVE PIXEL AND METHOD OF CONTROLLING RADIATION IMAGING APPARATUS

BACKGROUND

Field of the Disclosure

The present disclosure relates to a radiation imaging apparatus, a radiation imaging system, and a method of controlling a radiation imaging apparatus.

Description of the Related Art

Radiation imaging apparatuses having a function of monitoring irradiation of radiation are known. With this function, the radiation imaging apparatus can detect, for example, a timing at which irradiation of radiation from a radiation source was started, a timing at which the irradiation of radiation is to be stopped, and an irradiation amount or an integrated irradiation amount of radiation. Through detection of an integrated irradiation amount of radiation that has been transmitted through a subject and stopping of the irradiation of radiation by the radiation source at a time point when the detected integrated irradiation amount has reached an appropriate amount, automatic exposure control (AEC) is enabled. To achieve this function, there are known radiation imaging apparatus including pixels for detecting a radiation dose irradiated separately from pixels for taking a radiation image.

In Japanese Patent Application Laid-Open No. 2014-66689, there is disclosed a method in which, when a defect occurs in a dose detection pixel, a radiation dose cannot be detected appropriately, and hence the defect is extracted from a difference of two detection signals obtained with different accumulation times in dose detection pixels.

In the related art, the defect is extracted only in the dose detection pixels, and hence it is required to separately extract a defect in imaging pixels for taking the radiation image by a different method.

SUMMARY

It is an object of the present disclosure to provide a technology with which defective pixel information in taking a radiation image and defective pixel information in detecting a dose can be generated efficiently.

According to at least one embodiment, there is provided a radiation imaging apparatus including: a plurality of pixels arranged to convert radiation into an electric signal; and a generation unit configured to generate, based on the electric signal obtained as a result of the conversion by the plurality of pixels, first defective pixel information indicating a defective pixel in taking a radiation image of the plurality of pixels, and second defective pixel information indicating a defective pixel in detecting a dose of the plurality of pixels.

Further features of various embodiments will become apparent from the following description of exemplary embodiments with reference to the attached drawings.

DESCRIPTION OF THE EMBODIMENTS

Some example embodiments will now be described in detail in accordance with the accompanying drawings.

Figure 1:
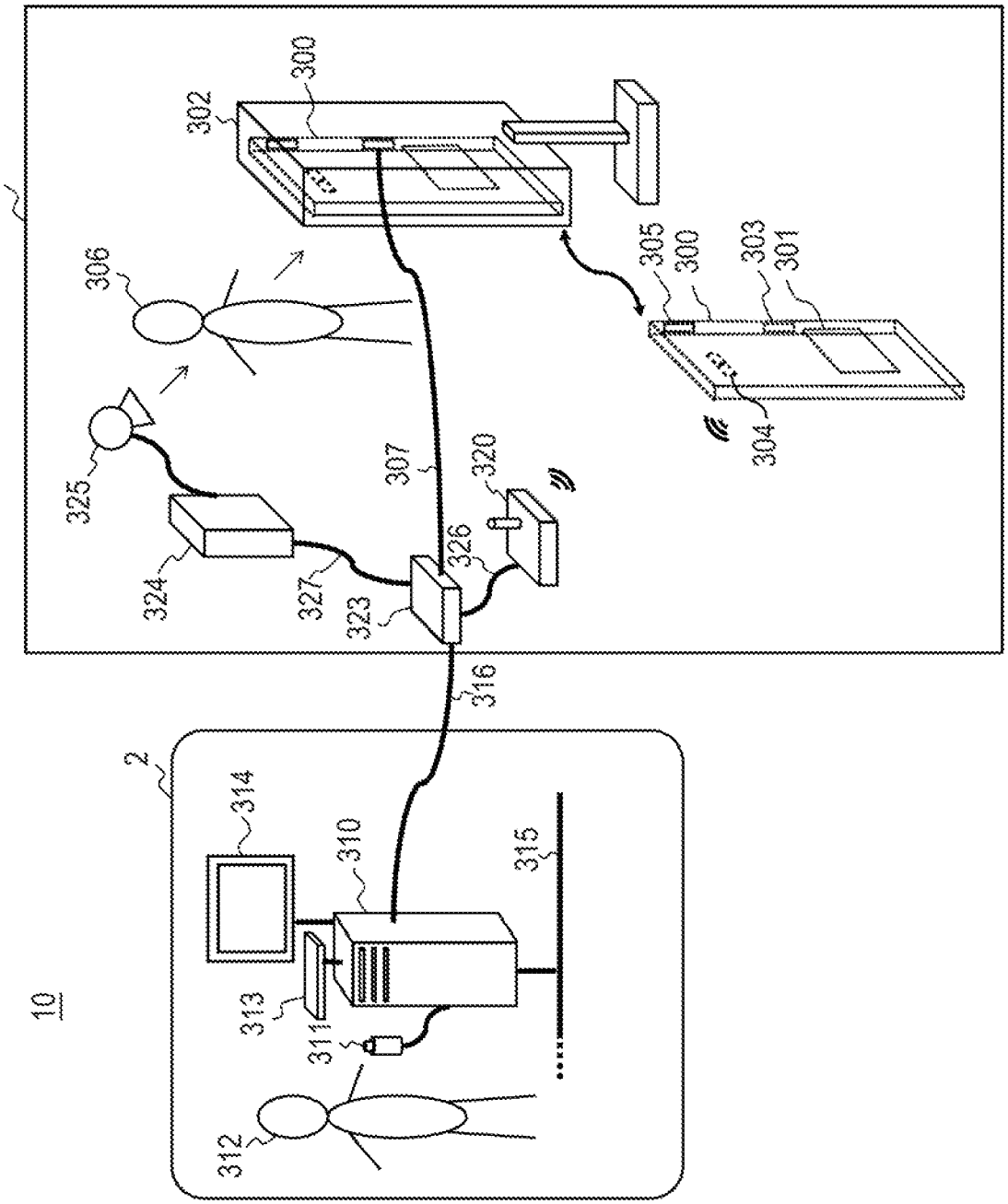
FIG. 1 is a diagram for illustrating a configuration example of a radiation imaging system according to at least one embodiment.

As illustrated in FIG. 1, a radiation imaging system 10 includes an imaging portion 1 and a control portion 2. The imaging portion 1 is configured to perform irradiation of radiation and radiation imaging. The radiation includes, in addition to an X-ray, an α-ray, a β-ray, a γ-ray, and various particle beams, for example.

The imaging portion 1 includes a radiation imaging apparatus 300, an upright stand 302, a communication cable 307, an access point (AP) 320, a communication control apparatus 323, a radiation generating apparatus 324, a radiation source 325, a communication cable 326, and a communication cable 327.

The control portion 2 includes a control apparatus 310, a radiation irradiation switch 311, an input apparatus 313, a display apparatus 314, a local area network (LAN) 315, and a communication cable 316.

The radiation imaging apparatus 300 includes a power supply control unit 301 formed of a battery, for example, a wired communication unit 303, a wireless communication unit 304, and a mounting detection unit 305, which is arranged to detect mounting of the radiation imaging apparatus 300 on the upright stand 302. The radiation imaging apparatus 300 is arranged to detect radiation that has been transmitted through a subject 306 to generate radiation image data.

The wired communication unit 303 is configured to communicate information by cable connection using a communication standard having a predetermined arrangement, or Ethernet (trademark) or other specifications. The wireless communication unit 304 includes a circuit board including an antenna and a communication IC, for example, and the circuit board is configured to perform wireless communication processing under a protocol based on a wireless LAN via an antenna. A frequency band, a specification, and a method of wireless communication in the wireless communication unit 304 are not limited, and may use NFC, Bluetooth (trademark), or other proximity wireless communication, or UWB or other methods. Further, the wireless communication unit 304 may have a plurality of wireless communication methods, and select one of the plurality of wireless communication methods as appropriate to perform communication.

The mounting detection unit 305 can be achieved by providing a contact detection element using a limit switch, for example, inductive or capacitive, magnetic proximity sensor, or other detection elements, or a signal to be electrically detected at the time of mounting. The mounting detection unit 305 is configured to detect that the radiation imaging apparatus 300 has been mounted on the upright stand 302.

The upright stand 302 is a rack on which the radiation imaging apparatus 300 is to be mounted so that a radiation image can be taken at an upright position. The radiation imaging apparatus 300 is removable from the upright stand 302, and is capable of taking an image both in a mounted state and a removed state.

The communication cable 307 is a cable for connecting the radiation imaging apparatus 300 and the communication control apparatus 323. The access point 320 is configured to perform wireless communication to/from the radiation imaging apparatus 300. The access point 320 is used to relay communication among the radiation imaging apparatus 300, the control apparatus 310, and the radiation generating apparatus 324 when the radiation imaging apparatus 300 is used while being removed from the upright stand 302. The radiation imaging apparatus 300 or the communication control apparatus 323 may include an access point. In that case, the radiation imaging apparatus 300, the control apparatus 310, and the radiation generating apparatus 324 may communicate to/from one another not via the access point 320 but via the access point of the radiation imaging apparatus 300 or the communication control apparatus 323. The communication control apparatus 323 is configured to perform control so that the access point 320, the radiation generating apparatus 324, and the control apparatus 310 communicate to/from one another.

The radiation generating apparatus 324 is configured to control the radiation source 325 so as to irradiate with radiation based on a predetermined irradiation condition. The radiation source 325 is an irradiation unit configured to irradiate the subject 306 with radiation under control of the radiation generating apparatus 324.

The communication cable 326 is a cable for connecting the access point 320 and the communication control apparatus 323. The communication cable 327 is a cable for connecting the radiation generating apparatus 324 and the communication control apparatus 323.

The control apparatus 310 is configured to communicate to/from the radiation generating apparatus 324 and the radiation imaging apparatus 300 via the communication control apparatus 323 and to exercise control over the radiation imaging system 10.

The radiation irradiation switch 311 is used to input a timing to start irradiation of radiation through operation by an operator 312. The input apparatus 313 is an apparatus to be used to input an instruction from the operator 312, and includes various input devices, such as a keyboard or a touch panel. The display apparatus 314 is an apparatus configured to display radiation image data that has been subjected to image processing and a GUI, and includes a display, for example.

The LAN 315 may be a backbone network in a hospital. The communication cable 316 is a cable for connecting the control apparatus 310 and the communication control apparatus 323.

Figure 2:
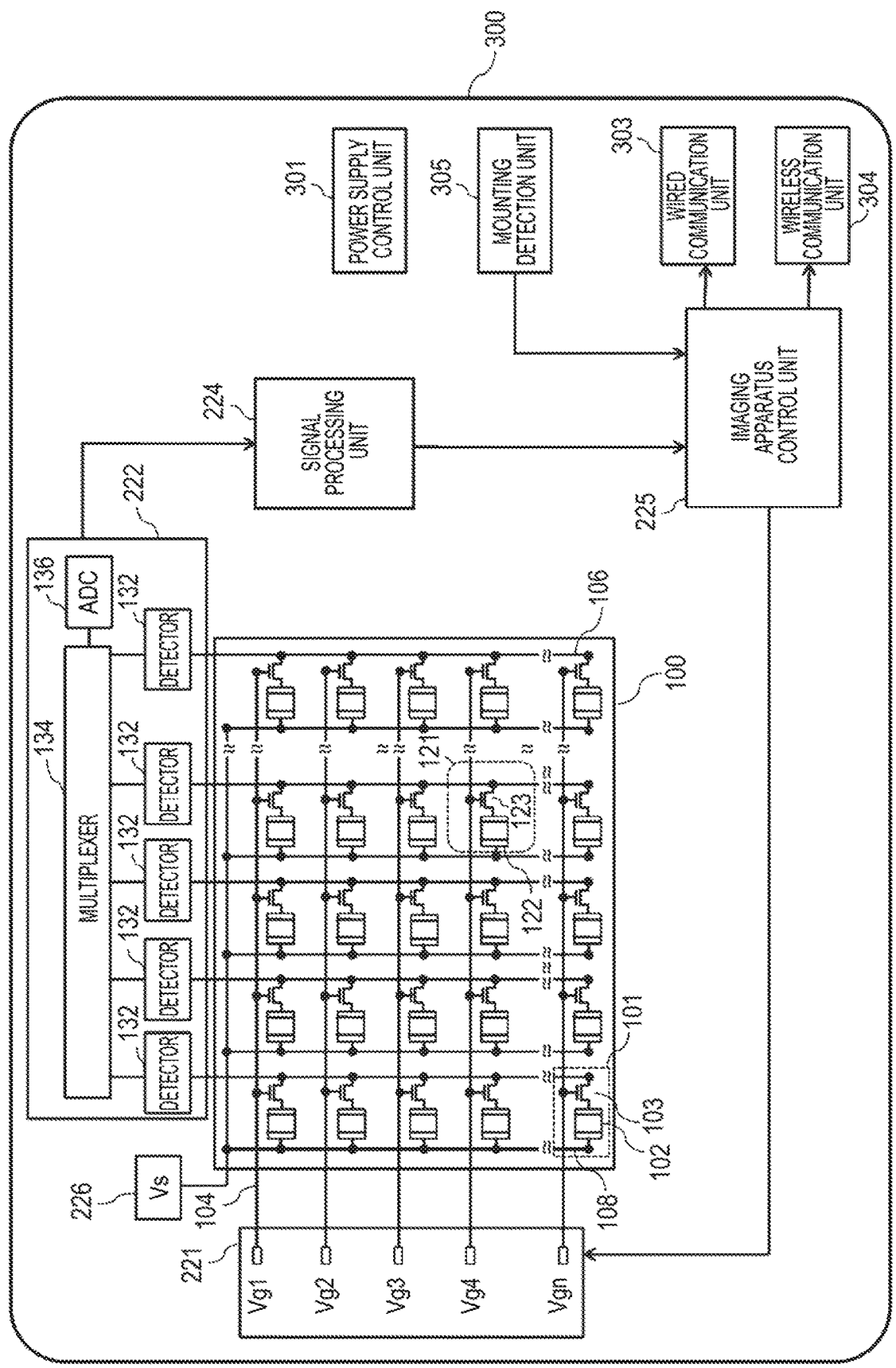
FIG. 2 is a diagram for illustrating a configuration example of a radiation imaging apparatus.

As illustrated in FIG. 2, the radiation imaging apparatus 300 includes a radiation detector 100, a drive circuit 221, a readout circuit 222, a signal processing unit 224, an imaging apparatus control unit 225, a power supply circuit 226, the power supply control unit 301, the wired communication unit 303, the wireless communication unit 304, and the mounting detection unit 305.

The radiation detector 100 includes a plurality of pixels arranged in matrix to detect irradiated radiation. In the following description, a region of the radiation detector 100 in which the plurality of pixels are arranged is referred to as an "imaging region". The plurality of pixels include a plurality of detection pixels 101 and a plurality of correction pixels 121, and are each configured to convert radiation into an electric signal. The detection pixels 101 are pixels for generating a radiation image or detect radiation. The correction pixels 121 are pixels for removing a dark current component or a crosstalk component.

Each of the plurality of detection pixels 101 includes a conversion element 102 and a switch 103. The conversion element 102 is arranged to convert radiation into the electric signal. The switch 103 is a switch for connecting a column signal line 106 and the conversion element 102.

The conversion element 102 includes a scintillator arranged to convert radiation into light, and a photoelectric conversion element arranged to convert light into an electric signal, to thereby convert radiation into the electric signal. The scintillator is formed as a sheet so as to cover the imaging region, and is shared by a plurality of pixels. The conversion element 102 may include a conversion element arranged to directly convert radiation into an electric signal, to thereby convert radiation into the electric signal.

The switch 103 includes a thin film transistor (TFT) having an active region formed of a semiconductor, for example, amorphous silicon or polysilicon (preferably, polysilicon).

Each of the plurality of correction pixels 121 includes a conversion element 122 and a switch 123. The conversion element 122 has a configuration similar to that of the conversion element 102, and is arranged to convert radiation into an electric signal. The switch 123 is a switch that has a configuration similar to that of the switch 103, and for connecting a column signal line 106 and the conversion element 122.

The correction pixel 121 has a configuration similar to the detection pixel 101. However, the detection pixel 101 has a region for detecting radiation that is wider than that of the correction pixel 121. When the correction pixel 121 has a direct conversion element 122 arranged to directly convert radiation into the electric signal, for example, a shielding member using a heavy metal, such as lead, is provided as a shielding member for shielding the radiation, on the conversion element 122 of the correction pixel 121.

When the correction pixel 121 includes a scintillator arranged to convert radiation into light and an indirect conversion element 122 arranged to convert the light into an electric signal, a shielding film made of aluminum, for example, is provided, as a shielding member for shielding the light, between the conversion element and the scintillator of the correction pixel 121.

Irrespective of whether the conversion element 122 is of the direct type or the indirect type, the correction pixel 121 has a shielding member arranged in a region at least partially overlapping the conversion element 122 of the correction pixel 121 in plan view of the imaging region.

The correction pixels 121 are shielded from radiation to detect the dark current component or the crosstalk component. The detection pixels 101 are arranged to output radiation information or a radiation image based on radiation. The signal processing unit 224 can generate correct radiation information or a correct radiation image by subtracting, from the radiation information or the radiation image output by the detection pixels 101, the dark current component or the crosstalk component output by the correction pixels 121.

Figure 3:
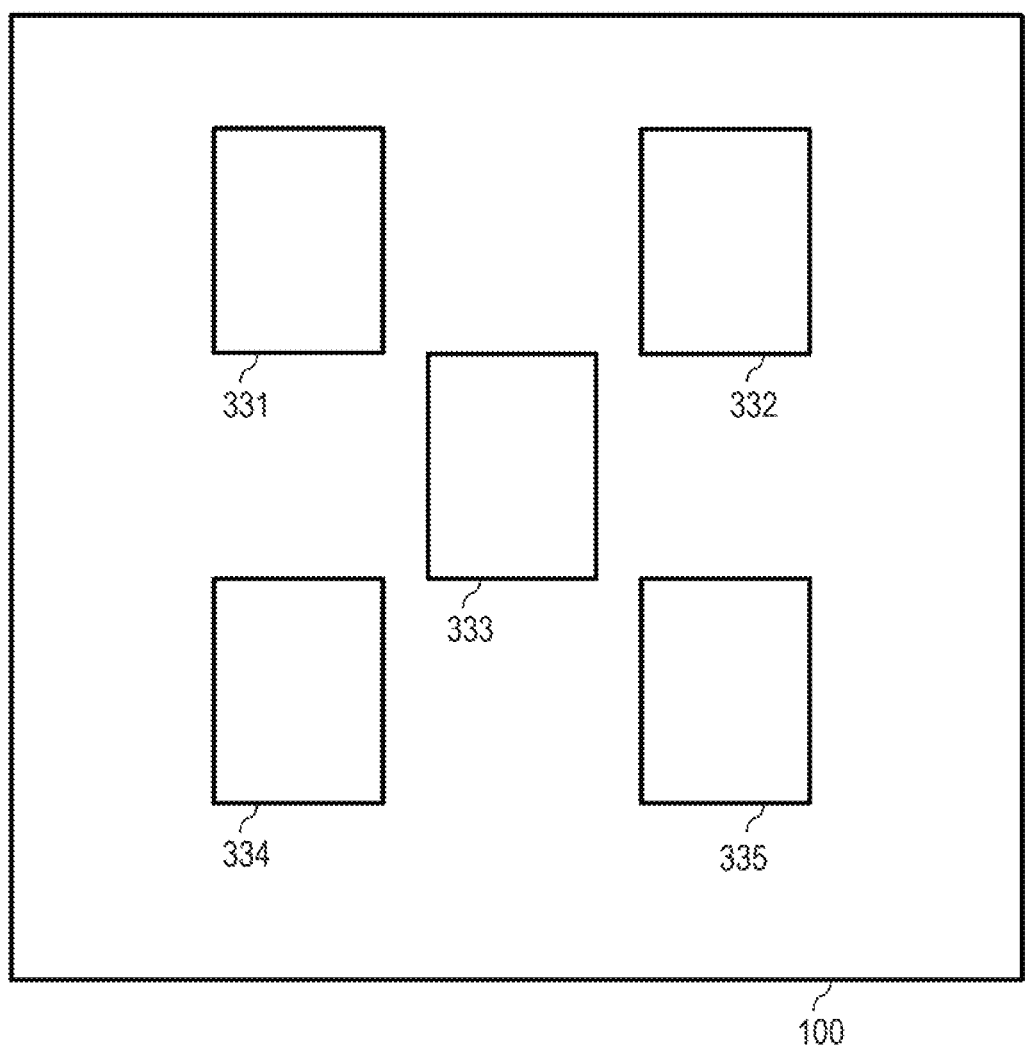
FIG. 3 is a diagram for illustrating an example of arrangement of regions of interest.

FIG. 3 is a diagram for illustrating an example of arrangement of a plurality of regions 331 to 335 of interest (ROI) in the radiation detector 100. The radiation detector 100 includes the detection pixels 101 and the correction pixels 121 in the regions 331 to 335 of interest, and includes the detection pixels 101 in regions other than the regions 331 to 335 of interest.

The radiation imaging apparatus 300 includes a plurality of column signal lines 106 and a plurality of drive lines 104. Each of the plurality of column signal lines 106 is connected in common to pixels in each column in the imaging region. Each of the plurality of drive lines 104 is connected in common to pixels in each row in the imaging region. The drive circuit 221 is arranged to supply voltages Vg1 to Vgn to the plurality of pixels for each row via the plurality of drive lines 104.

The conversion element 102 has a first electrode connected to a first main electrode of the switch 103. The conversion element 102 has a second electrode connected to a bias line 108. One bias line 108 extends in a column direction, and is connected in common to the second electrodes of a plurality of conversion elements 102 arrayed in the column direction. The switch 103 has a second main electrode connected to the column signal line 106.

The conversion element 122 has a first electrode connected to a first main electrode of the switch 123. The conversion element 122 has a second electrode connected to the bias line 108. One bias line 108 is connected in common to the second electrodes of the plurality of conversion elements 122 arrayed in the column direction. The switch 123 has a second main electrode connected to the column signal line 106.

The power supply circuit 226 is arranged to supply a bias voltage Vs to the bias line 108. The power supply control unit 301 includes a battery and a DC-DC converter, for example. The power supply control unit 301 includes the power supply circuit 226, and is arranged to generate a power supply voltage for an analog circuit, and a power supply voltage for a digital circuit arranged to perform drive control and communication, for example.

The second main electrodes of the switches 103 and 123 in each column are connected to the column signal line 106 in each column. Control electrodes of the switches 103 and the switches 123 in each row are connected to the drive line 104 in each row. The plurality of column signal lines 106 are connected to the readout circuit 222.

The readout circuit 222 includes a plurality of detection units 132, a multiplexer 134, and an analog-to-digital converter (hereinafter referred to as "AD converter") 136. The plurality of column signal lines 106 are connected to the plurality of detection units 132, respectively. One column signal line 106 is connected to one detection unit 132. The detection unit 132 includes, for example, a differential amplifier to amplify a signal of the column signal line 106. The multiplexer 134 is arranged to select the plurality of detection units 132 in predetermined order, and supply a signal from the selected detection unit 132 to the AD converter 136. The AD converter 136 is arranged to subject the supplied signal to analog-to-digital conversion and output a result.

The signal processing unit 224 is configured to output irradiated radiation information to the radiation imaging apparatus 300 based on the output signal from the AD converter 136. Specifically, the signal processing unit 224 is configured to subtract, from the radiation information or the radiation image generated by the detection pixels 101, the dark current component or the crosstalk component generated by the correction pixels 121.

The imaging apparatus control unit 225 is configured to perform detection of irradiation of radiation, calculation of an irradiation amount and an integrated irradiation amount of the radiation, and the like, based on the information from the signal processing unit 224. The imaging apparatus control unit 225 is configured to control the drive circuit 221, the readout circuit 222, and the like, based on the information from the signal processing unit 224 and a control command from the control apparatus 310 of FIG. 1. The imaging apparatus control unit 225 is also configured to transmit the information from the signal processing unit 224 to the control apparatus 310 via the wired communication unit 303 or the wireless communication unit 304.

Figure 4:
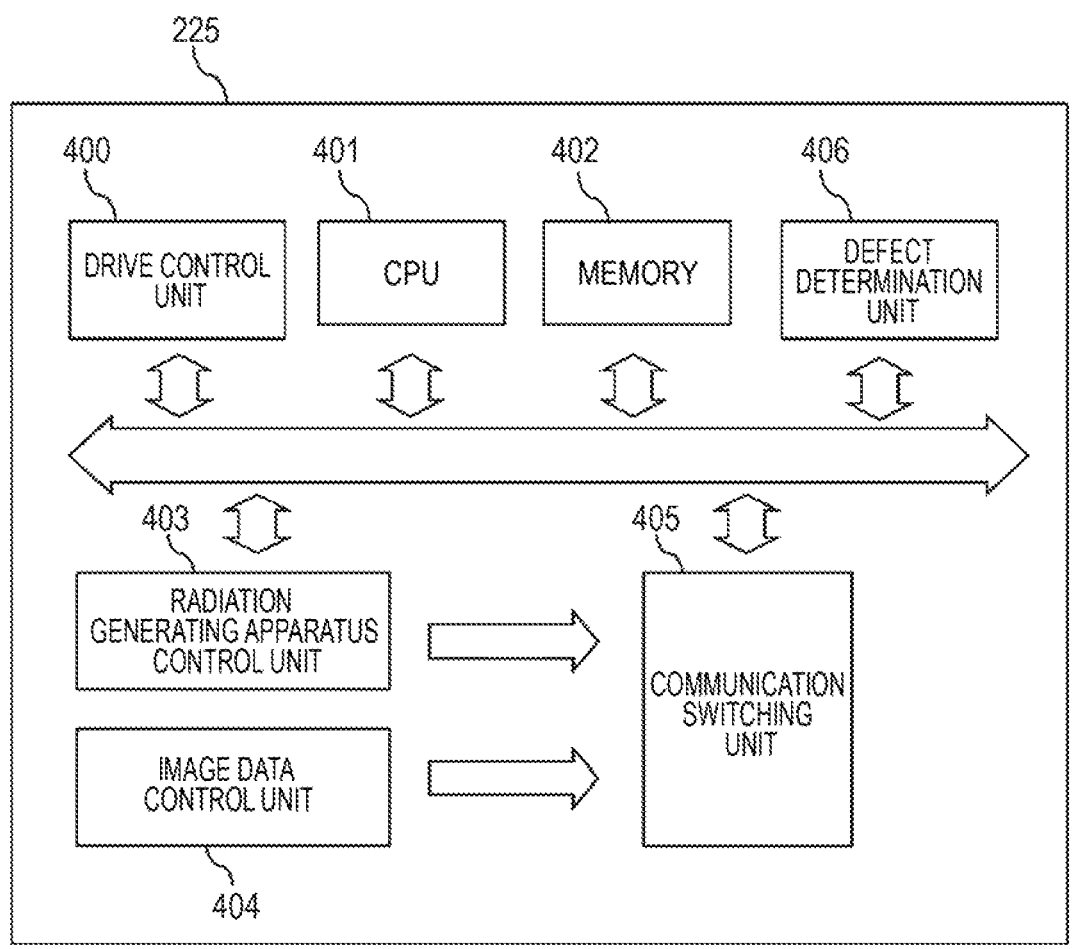
FIG. 4 is a diagram for illustrating a configuration example of an imaging apparatus control unit.

As illustrated in FIG. 4, the imaging apparatus control unit 225 includes a drive control unit 400, a CPU 401, a memory 402, a radiation generating apparatus control unit 403, an image data control unit 404, a communication switching unit 405, and a defect determination unit 406.

The drive control unit 400 is configured to control the drive circuit 221 and the readout circuit 222 based on the information from the signal processing unit 224 and the command from the control apparatus 310. The CPU 401 is configured to control the entire radiation imaging apparatus 300 using a program stored in the memory 402 and various kinds of data. The memory 402 stores the program to be executed by the CPU 401 and the various kinds of data, for example. The various kinds of data includes various kinds of data obtained by processing of the CPU 401 and the radiation image data.

The radiation generating apparatus control unit 403 is configured to control communication to/from the radiation generating apparatus 324 based on the information from the signal processing unit 224 and the information from the drive control unit 400. The radiation generating apparatus control unit 403 and the radiation generating apparatus 324 communicate information on the control of the radiation generating apparatus 324 (for example, notifications to start and stop irradiation of radiation, and the irradiation amount and the integrated irradiation amount of the radiation).

The image data control unit 404 is configured to store, in the memory 402, image data from the signal processing unit 224. The defect determination unit 406 is configured to determine, based on the image data stored in the memory 402, whether each of the plurality of detection pixels 101 is defective, and generate an image defect map and a dose detection defect map. The defect determination unit 406 is configured to store the image defect map and the dose detection defect map in the memory 402. The image data control unit 404 is configured to use the dose detection defect map stored in the memory 402 to perform defect correction on a detected dose. The image data control unit 404 is also configured to use the image defect map stored in the memory 402 to perform defect correction on the radiation image data. The defect correction is performed by removing data for pixels determined as a defective pixel from the detected dose data and image data. The image data control unit 404 is further configured to control communication to/from the control apparatus 310, and communicate the radiation image data and information on control (for example, control command).

The communication switching unit 405 is configured to enable communication by means of the wired communication unit 303 when the communication cable 307 is connected to the radiation imaging apparatus 300, and enables communication by means of the wireless communication unit 304 when the communication cable 307 is disconnected from the radiation imaging apparatus 300.

Next, operation of the radiation imaging system 10 during automatic exposure control (AEC) imaging is described. The operator 312 uses the input apparatus 313 to set, on the control apparatus 310, subject information, for example, an ID, a name, and a date of birth of the subject 306, and imaging information, for example, a part to be imaged of the subject 306.

The operator 312 uses the input apparatus 313 to input, to the control apparatus 310, a dose, a maximum irradiation time, a tube current, a tube voltage, a region of interest, and part information, for example. The control apparatus 310 transmits the input irradiation conditions of the radiation, the input region of interest, and the input part information, for example, to the radiation imaging apparatus 300 and the radiation generating apparatus 324.

When preparations for imaging are completed, the operator 312 pushes the radiation irradiation switch 311. When the radiation irradiation switch 311 is pushed, the radiation source 325 irradiates the subject 306 with radiation under control of the radiation generating apparatus 324. At that time, the radiation imaging apparatus 300 communicates to/from the radiation generating apparatus 324 to perform control to start the irradiation of radiation. The radiation with which the subject 306 is irradiated is transmitted through the subject 306 to enter the radiation imaging apparatus 300. The radiation imaging apparatus 300 drives the drive line 104 specified for each specified region of interest by the drive circuit 221. A plurality of detection pixels 101 corresponding to the specified drive line 104 detect doses (radiation amount), and output dose information. The imaging apparatus control unit 225 calculates an integrated irradiation amount, which is an integrated value of doses detected in a predetermined period by the detection pixels 101. The imaging apparatus control unit 225 calculates a target value of an appropriate dose based on the integrated irradiation amount from the signal processing unit 224, and the part information and imaging conditions, for example, input by the operator 312, to determine a timing to stop the irradiation of radiation. When the integrated irradiation amount has reached the target value, the radiation imaging apparatus 300 transmits a signal for stopping the irradiation of radiation to the radiation generating apparatus 324 via the communication cable 307, the communication control apparatus 323, and the communication cable 327. The radiation generating apparatus 324 stops, based on the received signal for stopping the irradiation of radiation, the irradiation of radiation by the radiation source 325.

After the irradiation of radiation is stopped, the detection pixels 101 convert radiation into an electric signal to generate a radiation image signal. The AD converter 136 converts an analog radiation image signal into digital radiation image data. The signal processing unit 224 subtracts the dark current component or the crosstalk component from the radiation image data to generate correct radiation image data. The imaging apparatus control unit 225 transmits the generated digital radiation image data to the control apparatus 310 via the communication cable 307, the communication control apparatus 323, and the communication cable 316.

The control apparatus 310 subjects the received radiation image data to image processing. The control apparatus 310 displays, on the display apparatus 314, a radiation image based on the radiation image data that has been subjected to the image processing. The control apparatus 310 also serves as an image processing apparatus and a display control apparatus.

A method of determining a defect in a pixel is described with reference to FIG. 5.

In S501, in response to an instruction from the control apparatus 310, the radiation imaging apparatus 300 generates (acquires), based on the electric signal obtained by conversion by a plurality of pixels, dark images of a plurality of frames for use in determining a defect. Specifically, under a state in which no radiation is irradiated by the radiation source 325, the radiation imaging apparatus 300 generates dark images of the plurality of frames (for example, 100 frames) using the detection pixels 101, and offset correction images using the correction pixels 121. Next, the radiation imaging apparatus 300 generates corrected images of, for example, 100 frames by subtracting the offset correction images from the dark images to store the corrected images in the memory 402.

In S502, the CPU 401 calculates, based on the corrected images of 100 frames stored in S501, an average value AVE and a standard deviation "σ" of values of each pixel in the corrected images of 100 frames.

In S503, the defect determination unit 406 determines whether each of a plurality of pixels is a defective pixel in taking the radiation image with use of a first determination criterion. Specifically, the defect determination unit 406 determines whether each pixel is the defective pixel based on the average value AVE and the standard deviation "σ" of each pixel that have been calculated in S502.

Specifically, the defect determination unit 406 determines that a pixel having the average value AVE equal to or higher than a first threshold, or the standard deviation "σ" equal to or higher than a third threshold is the defective pixel, and determines that a pixel having the average value AVE lower than the first threshold, and the standard deviation "σ" lower than the third threshold is not the defective pixel. For example, the first threshold is 100, and the third threshold is 40.

The defect determination unit 406 may determine whether each pixel is a defective pixel based on a maximum value of 100 frames of each pixel. Further, the defect determination unit 406 determines whether each pixel is the defective pixel based on the corrected images, but some embodiments are not limited thereto. The defect determination unit 406 may determine whether each pixel is the defective pixel based on a dark image before the correction, or an image that has been corrected for gain. In other words, the images of the plurality of frames in S501 are images of the plurality of frames taken with use of the plurality of pixels, or images of a plurality of frames obtained by correcting the images of the plurality of frames taken with use of the plurality of pixels.

In S504, the defect determination unit 406 generates the image defect map (defective pixel information) indicating the defective pixel in taking the radiation image of the plurality of pixels based on the result of the determination in S503, and stores the image defect map in the memory 402. For example, the image defect map indicates whether each pixel is a defective pixel. The defect determination unit 406 generates the image defect map at the time of shipping or during maintenance of the radiation imaging apparatus 300. Further, when a previous image defect map is stored in the memory 402, the defect determination unit 406 deletes the previous image defect map, and stores the image defect map that is generated this time in the memory 402.

The image data control unit 404 performs defect correction on the taken radiation image data based on the image defect map stored in the memory 402.

In S505, the defect determination unit 406 determines whether each pixel in a row forming the regions 331 to 335 of interest is a defective pixel in detecting the dose with use of a second determination criterion, which is different from the above-mentioned first determination criterion. Specifically, the defect determination unit 406 determines whether each pixel in the row forming the regions 331 to 335 of interest is the defective pixel based on the average value AVE and the standard deviation "σ" of each pixel that have been calculated in S502. The radiation imaging apparatus 300 detects the doses and calculates the integrated irradiation amount in a shorter period of time when detecting the dose than when the radiation image data is generated, and hence a large difference in average value AVE or a large standard deviation "σ" affects accuracy of detecting the dose. Therefore, the second determination criterion in S505 is stricter than the first determination criterion in S503.

Specifically, the defect determination unit 406 determines that a pixel having the average value AVE equal to or higher than a second threshold, or the standard deviation "σ" equal to or higher than a fourth threshold is the defective pixel, and determines that a pixel having the average value AVE lower than the second threshold, and the standard deviation "σ" of lower than the fourth threshold is not the defective pixel. The second threshold is a value that is different from the above-mentioned first threshold, and the fourth threshold is a value that is different from the above-mentioned third threshold. For example, the second threshold is 50, and the fourth threshold is 20. The second threshold of "50" is lower than the first threshold of "100". The fourth threshold of "20" is lower than the third threshold of "40".

For example, the defect determination unit 406 determines that a pixel having the average value AVE equal to or higher than 50, or the standard deviation "σ" equal to or higher than 20 is the defective pixel, and determines that a pixel having the average value AVE lower than 50, and the standard deviation "σ" lower than 20 is not the defective pixel.

Figure 6:
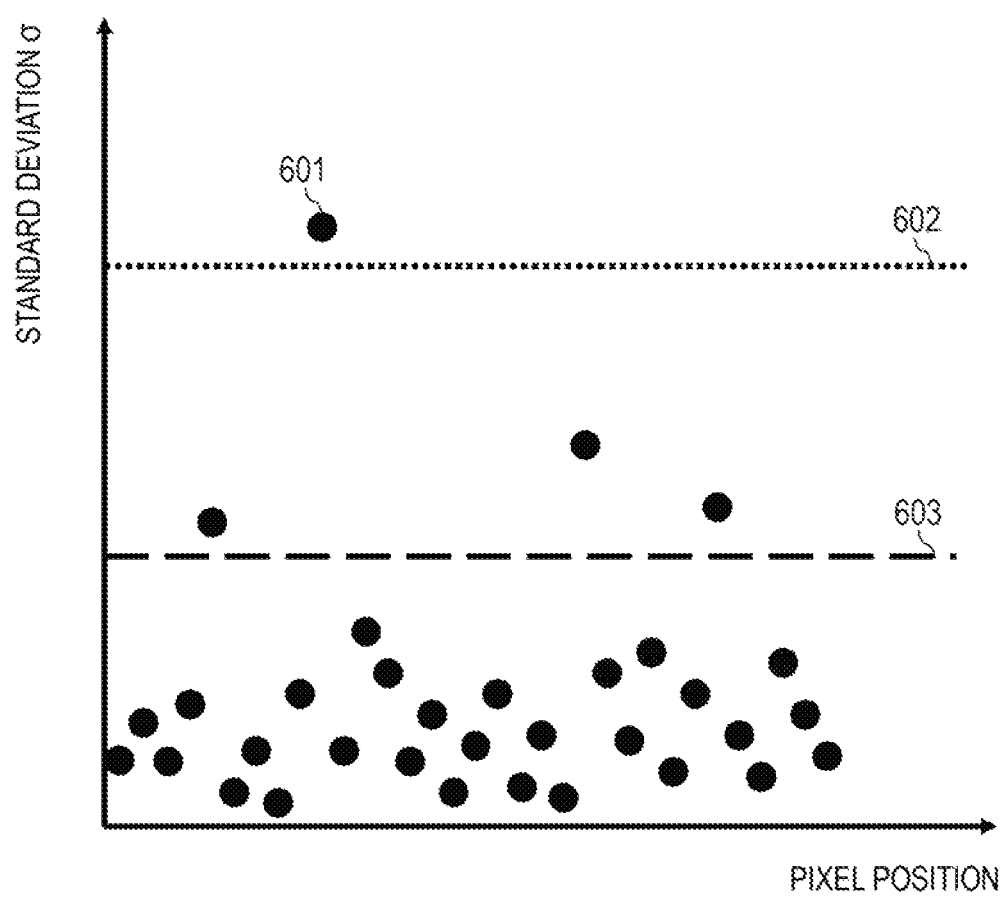
FIG. 6 is a graph for showing a relationship between a pixel position and a standard deviation.

In FIG. 6, a standard deviation 601 indicates a value of the standard deviation "σ" of values of 100 frames for each pixel. A determination criterion 602 is a standard deviation of the determination criteria in S503, and is 40, for example. A determination criterion 603 is a standard deviation of the determination criteria in S505, and is 20, for example. In S503, the defect determination unit 406 determines that each pixel is the defective pixel when the standard deviation "σ" of each pixel is equal to or higher than the determination criterion 602. In S505, the defect determination unit 406 determines that each pixel is the defective pixel when the standard deviation "σ" of each pixel is equal to or higher than the determination criterion 603.

In S506, the defect determination unit 406 generates, based on a result of the determination in S505, a dose detection defect map (defective pixel information) indicating the defective pixel in detecting the dose of the plurality of pixels, and stores the dose detection defect map in the memory 402. For example, the dose detection defect map indicates whether each pixel of a row forming the regions 331 to 335 of interest is a defective pixel. The defect determination unit 406 generates the dose detection defect map at the time of shipping or during maintenance of the radiation imaging apparatus 300. Further, when a previous dose detection defect map is stored in the memory 402, the defect determination unit 406 deletes the previous dose detection defect map, and stores the dose detection defect map that is generated this time in the memory 402.

Next, operation of the radiation imaging system 10 during the AEC imaging is described. The image data control unit 404 corrects, with use of the dose detection defect map, doses detected with use of some pixels (pixels in the regions of interest) of the plurality of pixels, and performs, when an integrated value of the corrected doses has reached the target value, control so as to stop the irradiation of radiation by the radiation source 325. Thereafter, the image data control unit 404 corrects, with use of the image defect map, the radiation image taken with use of the plurality of pixels.

As described above, the defect determination unit 406 can generate the image defect map and the dose detection defect map with high accuracy based on the corrected images. The image data control unit 404 performs defect correction on the detected doses based on the dose detection defect map, and performs defect correction on the taken radiation image data based on the image defect map.

The processing of S501 and S502 is not limited to the above-mentioned processing, but may be the following processing. In S501, under a state in which the radiation imaging apparatus 300 is irradiated with radiation by the radiation source 325, the radiation imaging apparatus 300 may generate radiation images of a plurality of frames using the detection pixels 101, and offset correction images using the correction pixels 121. In that case, the radiation imaging apparatus 300 generates corrected images of the plurality of frames by subtracting the offset correction images from the radiation images to store the corrected images in the memory 402.

In S502, the CPU 401 calculates, based on the corrected images of the plurality of frames stored in S501, the average value AVE and the standard deviation "σ" of the values of the plurality of frames for each pixel.

Further, the radiation imaging apparatus 300 may calculate the average value AVE and the standard deviation "σ" of the values of each pixel based on images of a plurality of imaging modes (for example, modes with different sizes by binning, modes with different sensor gains, perspective modes, or consecutive imaging modes).

Figure 5:
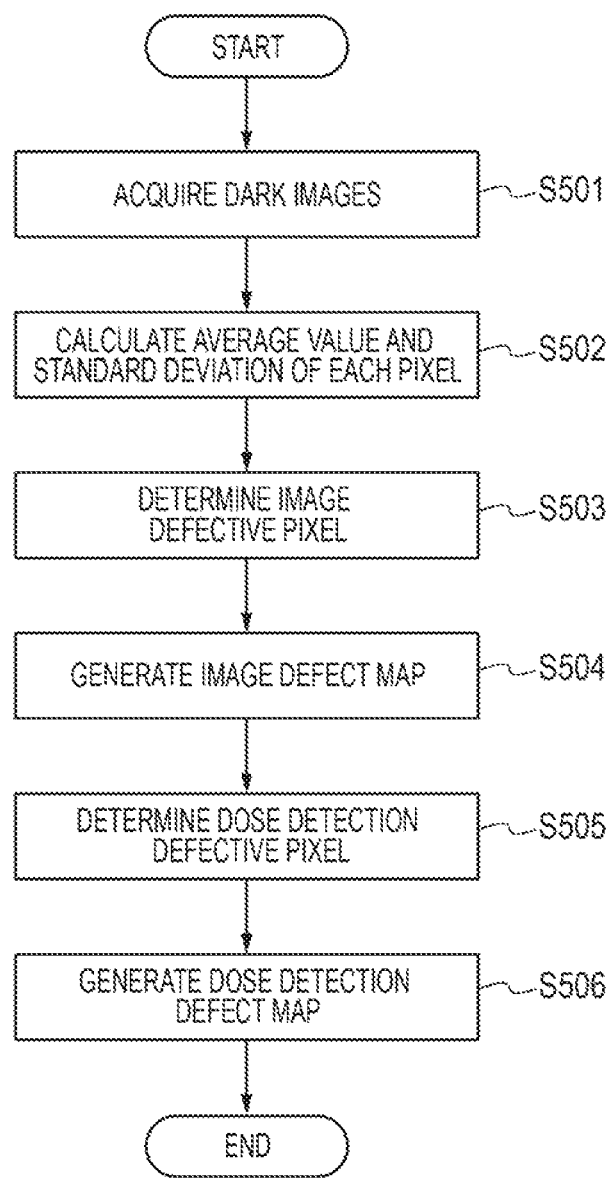
FIG. 5 is a flow chart for illustrating a method of controlling the radiation imaging system.

Further, in the processing illustrated in FIG. 5, a timing to start the next processing may be determined based on results of the previous and current processing. For example, when the current number of defective pixels is increased by a threshold or more with respect to the previous number of defective pixels, the radiation imaging apparatus 300 schedules the processing to start after a day. Further, when the current number of defective pixels is not increased by the threshold or more with respect to the previous number of defective pixels, the radiation imaging apparatus 300 schedules the processing to start after a month.

OTHER EMBODIMENTS

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the embodiments described above, positional information for the defective pixel in taking the radiation image and the defective pixel in detecting the dose can be generated efficiently.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2019-019733, which was filed on Feb. 6, 2019 and which is hereby incorporated by reference herein in its entirety.

What is claimed is:

1. A radiation imaging apparatus comprising:
   a plurality of pixels arranged to convert radiation into an electric signal; and
   a processor coupled to a storage medium and programmed to function as a generation unit configured to generate, based on the electric signal obtained as a result of a conversion of the radiation by the plurality of pixels, first defective pixel information indicating a defective pixel in taking a radiation image among the plurality of pixels, and second defective pixel information indicating a defective pixel in detecting a dose among the plurality of pixels.

2. The radiation imaging apparatus according to claim 1, wherein the generation unit is configured to use a first determination criterion to determine whether a pixel of the plurality of pixels is the defective pixel in taking the radiation image, and use a second determination criterion, which is different from the first determination criterion, to determine whether the pixel of the plurality of pixels is the defective pixel in detecting the dose.

3. The radiation imaging apparatus according to claim 2, wherein the second determination criterion is stricter than the first determination criterion.

4. The radiation imaging apparatus according to claim 1, wherein the generation unit is configured to generate the first defective pixel information and the second defective pixel information based on images of a plurality of frames generated based on electric signals of the plurality of pixels.

5. The radiation imaging apparatus according to claim 4, wherein the images of the plurality of frames are one of: images of a plurality of frames taken with a use of the plurality of pixels; and images of a plurality of frames obtained by correcting the images of the plurality of frames taken with a use of the plurality of pixels.

6. The radiation imaging apparatus according to claim 4, wherein the images of the plurality of frames are images taken when a radiation source stops an irradiation of radiation.

7. The radiation imaging apparatus according to claim 4, wherein the images of the plurality of frames are images taken when a radiation source performs an irradiation of radiation.

8. The radiation imaging apparatus according to claim 4, wherein the generation unit is configured to generate the first defective pixel information and the second defective pixel information based on an average value of values of each pixel in the images of the plurality of frames.

9. The radiation imaging apparatus according to claim 8, wherein the generation unit is configured to determine that a pixel of the plurality of pixels is the defective pixel in taking the radiation image when an average value of values of the pixel is equal to or higher than a first threshold, and that a pixel of the plurality of pixels is the defective pixel in detecting the dose when an average value of values of the pixel is equal to or higher than a second threshold, the second threshold being different from the first threshold.

10. The radiation imaging apparatus according to claim 9, wherein the second threshold is lower than the first threshold.

11. The radiation imaging apparatus according to claim 4, wherein the generation unit is configured to generate the first defective pixel information and the second defective pixel information based on a standard deviation of values of each pixel in the images of the plurality of frames.

12. The radiation imaging apparatus according to claim 11, wherein the generation unit is configured to determine that a pixel of the plurality of pixels is the defective pixel in taking the radiation image when a standard deviation of values of the pixel is equal to or higher than a third threshold, and that a pixel of the plurality of pixels is the defective pixel in detecting the dose when a standard deviation of values of the pixel is equal to or higher than a fourth threshold, the fourth threshold being different from the third threshold.

13. The radiation imaging apparatus according to claim 12, wherein the fourth threshold is lower than the third threshold.

14. The radiation imaging apparatus according to claim 4, wherein the generation unit is configured to generate the first defective pixel information and the second defective pixel information based on one of an average value and a standard deviation of values of each pixel in the images of the plurality of frames.

15. The radiation imaging apparatus according to claim 14, wherein the generation unit is configured to:
   determine that a pixel of the plurality of pixels is the defective pixel in taking the radiation image when an average value of values of the pixel is equal to or higher than a first threshold, or when a standard deviation of the values of the pixel is equal to or higher than a third threshold; and
   determine that a pixel of the plurality of pixels is the defective pixel in detecting the dose when an average value of values of the pixel is equal to or higher than a second threshold, the second threshold being different from the first threshold, or when a standard deviation of the values of the pixel is equal to or higher than a fourth threshold, the fourth threshold being different from the third threshold.

16. The radiation imaging apparatus according to claim 15, wherein the second threshold is lower than the first threshold, and the fourth threshold is lower than the third threshold.

17. The radiation imaging apparatus according to claim 1, wherein the processor further programmed to function as a control unit configured to correct doses detected with a use of some pixels of the plurality of pixels by using the second defective pixel information, and correct a radiation image taken with a use of the plurality of pixels by using the first defective pixel information.

18. The radiation imaging apparatus according to claim 17, wherein the control unit is further configured to control a radiation source to stop an irradiation of radiation if an integrated value of the doses after the correction has reached a target value, and then correct the radiation image taken with a use of the plurality of pixels.

19. A radiation imaging system comprising:
- a radiation imaging apparatus according to claim 1;
- a radiation source arranged to perform an irradiation of radiation; and
- a control apparatus configured to control the radiation imaging apparatus and the radiation source.

20. A method of controlling a radiation imaging apparatus, the radiation imaging apparatus including a plurality of pixels arranged to convert radiation into an electric signal, the method comprising:
- generating, based on the electric signal obtained as a result of a conversion of the radiation by the plurality of pixels, first defective pixel information indicating a defective pixel in taking a radiation image among the plurality of pixels, and second defective pixel information indicating a defective pixel in detecting a dose among the plurality of pixels.

\* \* \* \* \*